United States Patent [19]

Gracey

[11] 4,184,359

[45] Jan. 22, 1980

[54] GAS MONITOR FOR LIQUID FLOW LINE

[75] Inventor: Charles M. Gracey, Carmichael, Calif.

[73] Assignee: Aerojet-General Corporation, La Jolla, Calif.

[21] Appl. No.: 937,918

[22] Filed: Aug. 30, 1978

[51] Int. Cl.² ............................................. G01N 7/14
[52] U.S. Cl. ...................................................... 73/19
[58] Field of Search ................... 73/19, 64.2, 195, 200; 55/165, 168, 169, 170, 270; 137/12, 171, 210

[56] References Cited

U.S. PATENT DOCUMENTS

| | | | |
|---|---|---|---|
| 1,622,715 | 3/1927 | Hawxhurst | 73/200 |
| 2,745,282 | 5/1956 | Rochon | 73/19 |
| 2,882,995 | 4/1959 | Smith | 55/168 |
| 3,263,491 | 8/1966 | Brown et al. | 73/64.2 |
| 3,416,547 | 12/1968 | Glenn et al. | 137/12 |
| 3,435,595 | 4/1969 | Skelton | 55/169 |
| 3,707,983 | 1/1973 | Butler | 73/200 |

Primary Examiner—Stephen A. Kreitman
Attorney, Agent, or Firm—John S. Bell

[57] ABSTRACT

A device for measuring the concentrations of entrained and/or dissolved gases in a liquid flow, that includes a gas/liquid separating chamber, probes for monitoring depression of the liquid level in that chamber by separated gases, a regulator for providing a pressure drop that releases dissolved gases from incoming liquid, and a gage for measuring the liquid flow out of that chamber, is described herein.

3 Claims, 1 Drawing Figure

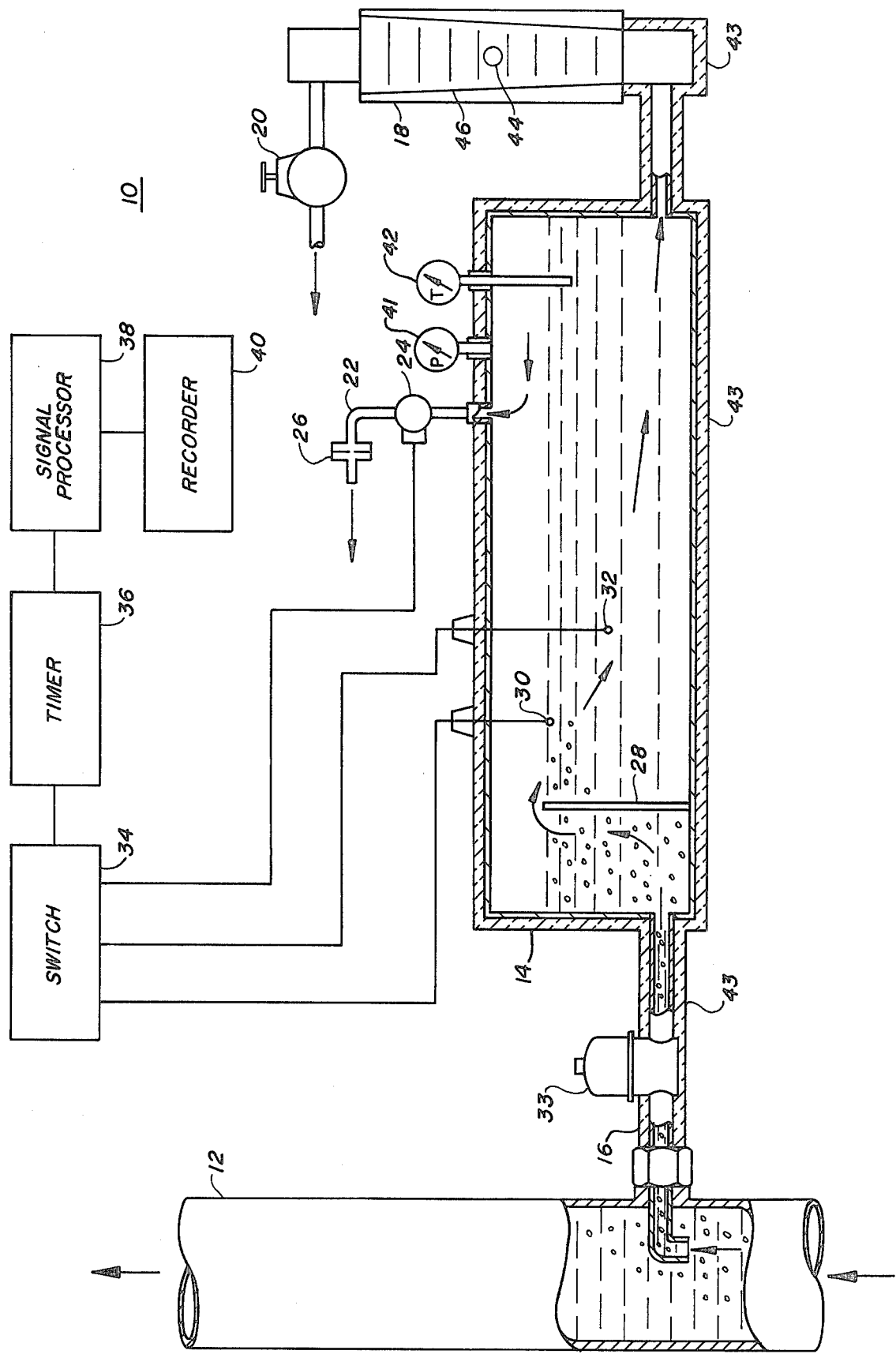

GAS MONITOR FOR LIQUID FLOW LINE

BACKGROUND OF THE INVENTION

1. Field of the Invention

Measurement of gas concentration in flowing liquids.

2. Brief Description of the Prior Art

It is important for both normal process control and identification of unusual conditions that may require shutdown or other special action in oil and geothermal well systems and many chemical processes, to know the concentration of gases in liquid flow. It is difficult to measure mixed gas/liquid flows directly because changes in the relative gas/liquid proportions of such flows are not readily distinguishable from changes in the flow rate. If the gas and liquid portions of a mixed flow are separated, it is difficult to monitor the gas flow directly without introducing temperature or pressure changes that produce erroneous measurements.

In one prior art device for logging the concentration of combustible gases in oil well drilling liquid, for example, gases separated from the drilling liquid are combined with a reference air flow, that is then directed to meters for measurement of the total volume and combustible percentage of the flow. If the air flow is not at the same temperature as the separated gases it will change the temperature and apparent volume of those gases so that subsequent measurements will not be accurate. Because of these difficulties, gas concentrations are now most commonly determined by taking samples of liquids and any gases carried by those liquids to a laboratory for chemical analysis. This requires substantial time, during which there may be temperature and/or pressure changes. And, the chemical tests now used identify only the total quantity of gas contained in a liquid, not the relative portions of dissolved and entrained gases.

SUMMARY OF THE INVENTION

This invention provides a meter suitable for immediate on-line measurement of the concentration of gas in a liquid flow, without any temperature variation, chemical reaction, or reference flow that could produce erroneous reading. Gas concentrations are determined from direct measurement of factors that are relatively easy to monitor, namely the liquid level in a gas/liquid separating chamber, and liquid flow out of that chamber. The rate at which the liquid level is depressed by released gases is proportional to the quantity of gas carried by the liquid flow. The liquid flow required for release of a particular quantity of gas is inversely proportional to the quantity of gas carried by that liquid. The monitoring of these two factors provides a complete indication of gas concentration.

The meter illustrated herein includes a regulator for providing a pressure drop in the input line to the gas/liquid separating chamber that releases gases dissolved in the incoming liquid from solution. If the composition and solubility of incoming liquid is known, the total quantity of dissolved gas can be determined in a single test from the quantity of gas released by one drop to a predetermined reference pressure. The relative quantities of gas dissolved and entrained, or in other words carried by but not dissolved in, the liquid are provided by comparison of measurements made with and without a pressure drop in the incoming liquid. If the gas solubility constant of the liquid is not known, the total quantity of dissolved gases can be determined from successive tests in which pressure is dropped to different values, and the qualities of gas brought out of solution at each of those values are compared mathematically utilizing the relationship between solubility and partial gas pressure known to those skilled in this art as Henry's law, or other appropriate mathematic formulae.

BRIEF DESCRIPTION OF THE DRAWING

The FIGURE provides a schematic illustration of a meter suitable for measuring gas concentration in a high temperature and pressure iquid flow such as the flow from a geothermal well.

DETAILED DESCRIPTION OF THE DRAWING

The FIGURE illustrates a meter 10 for measuring the concentration of gas in liquid flow through a pipeline 12. The meter 10 includes a gas/liquid separating chamber 14, a probe conduit 16 for supplying a portion of the flow through line 12 to separating chamber 14, a volumetric flow rate meter 18 for measuring the rate of liquid flow out of chamber 14, a valve 20 for controlling the rate of that output liquid flow, and a gas exhaust line 22 from chamber 14 controlled by a solenoid valve 24 and orifice 26. A baffle 28 for separating entrained air bubbles from the incoming liquid, and two liquid level detecting probes 30 and 32 are disposed in chamber 14. And, an adjustable pressure regulator 33 is disposed in line 16 to provide a pressure drop in that line 16 for measurement of dissolved gas concentrations.

The meter 10 also further includes a switch 34 responsive to signals from probes 30 and 32 for controlling solenoid valve 24 and timer 36, and a signal processor 38 and recorder 40 connected to timer 36 to provide gas concentration output signals. A pressure gage 41 and temperature gage 42 are included on chamber 14 for use in presetting meter 10 and determining the concentration of dissolved gas in a liquid flow. And, separating chamber 14, probe line 16, and liquid flow meter 18 are covered by a layer 43 f insulation so that no errors will be introduced by cooling of the fluid during measurement. One advantage of the design 10 is that it can be constructed to be reliable and durable, and provide accurate measurements using relatively inexpensive and uncomplicated components. Meter 18 for example is a straightforward design comprised of a ball 44 in a tapered tube 46 that is raised to an elevation in that tube proportional to the rate of flow therethrough.

To begin operation, the sampling probe 16 is fastened to the flow line 12, and valve 20 is adjusted to set a desired rate of liquid flow through chamber 14. This liquid flow rate should be sufficiently slow so that there will not be a wave action in chamber 14 that would cause erroneous measurements, and so that gas bubbles carried by the flow into that chamber will have time to separate from the liquid. Generally, a liquid flow rate less than about two feet per minute, and stay time in chamber 14 of about 1 or 2 minutes provides complete separation. When the concentration of gases entrained in the liquid flow is to be measured, regulator 33 is set to allow free flow without any pressure drop through line 16, and the flow rate as adjusted by valve 20 is further selected so that the pressure in chamber 14 will be equal to that in line 12. There is thus no pressure drop that would permit dissolved gases to leave solution and be erroneously identified as entrained gases. The rate established by valve 20 and indicated by meter 18 is supplied to signal processor 38. In the embodiment 10, that is accomplished by hand setting of processor 38. In other embodiments having a more sophisticated meter 18 and processor 38, the processor could be connected to receive signals from the flow meter automatically.

When the initial adjustment of meter 10 is complete and the liquid level in chamber 14 reaches the level established by probe 30, switch 34 closes solenoid valve 24 to stop air exhaust from chamber 14 and activates timer 36. When gas exhaust line 22 is closed, the volumetric rate of liquid flow out of chamber 14 indicated by meter 18 is equal to the total volumetric flow of liquid and gas into that chamber. The rate of that liquid outlet flow, and the time required for release of sufficient gas to depress the liquid level in chamber 14 to the elevation defined by probe 32 are both inversely proportional to the concentration of gas in liquid flow. And, those two values provide a complete indication of gas concentration. That is, either the time or the flow rate or both, required for release of sufficient gas to fill a pre-determined portion of chamber 14 will be larger for liquids carrying low gas concentrations and for liquids carrying higher concentrations. Signal processor 38 can therefore identify gas concentration by providing the product of the collection time and liquid flow rate to recorder 44. Or, that product can be divided into the fixed volume comprised of the portion of chamber 14 between the elevations defined by probes 30 and 32, to provide a value that is equal to, rather than inversely proportional to, the ratio of the gas volume to the total volume of a flow.

When the level of liquid in chamber 14 is depressed to the elevation defined by probe 32, a signal from that probe causes switch 34 to stop timer 36 and open solenoid valve 24 so that gas will be exhausted from that chamber and the liquid level raised for a subsequent measurement. Control orifice 26 prevents gas from being exhausted from chamber 14 at such a fast rate that waves that would produce erroneous readings would be created in chamber 14 or that there would be a large pressure drop in chamber 14. It is important to avoid large pressure drops when the meter 10 is used to monitor flow of geothermal well water or other liquids at elevated temperatures and pressures that would vaporize if pressures were reduced. When the liquid in chamber 14 reaches the level defined by probe 32 signals to switch 34 begin another measurement. If the meter 10 is used for on line monitoring of a flow, successive measurements will generally follow each other immediately.

Measurement of dissolved gases is similar to that of entrained gases, except that regulator 33 is preset to provide a pressure drop in line 16 that will release at least a portion of those gases from solution, and signal processor 38 is set to calculate dissolved gas concentration utilizing the following formula:

$$y = AP_g + B\left(\frac{x}{1-x}\right)P_g$$

where:

The above formula is derived from Henry's law, which states that at a given temperature, the partial gas pressure $P_g$ of gas in a mixed gas/liquid flow is proportional to the concentration of gas dissolved in a liquid.

y = the concentration of gas in liquid flow through pipeline 12.

A and B = system constants determined by simultaneous solution of the above equation for the different values obtained by setting regulator 33 to introduce different pressure drops into line 16 in successive tests.

$P_g$ = the difference between the total gas pressure $P_M$ measured by gage 41 and the vapor pressure $P_v$ of liquid in chamber 14.

$P_v$ = a physical property dependent upon the temperature and composition of the liquid.

x = ratio of the volumetric rate of gas collection (i.e. fixed collection volume in chamber 14 divided by collection time) to the volumetric rate of total flow (i.e. as indicated by meter 18).

Having thus provided this description, it will be apparent that many different devices are known for performing each of the functions of the different components of the meter 10, and can be used in different embodiments.

Therefore, what is claimed is:

1. A meter for identifying the concentration of gas in a liquid flow comprising:
a gas/liquid separating chamber having an inlet for receiving a liquid and any gas carried by that liquid, a gas outlet, and a liquid outlet;
a control valve for blocking flow through said gas outlet so that separated gas will collect and depress the level of liquid in said separating chamber;
means for measuring liquid flow out of said chamber; and
means for measuring separated gas by monitoring the liquid level in said separating chamber.

2. The meter of claim 1 further including:
a probe line for supplying liquid from a main pipeline to said separating chamber inlet;
a means for providing a pressure drop in said probe line to bring gas dissolved in said liquid out of solution; and
means for measuring pressure and temperature in said separating chamber to provide values for use in determining dissolved gas concentration.

3. The meter of claim 1 in which:
said liquid flow measuring means comprise a meter for measuring the volumetric rate of liquid flow from said separating chamber, which liquid flow equals the total flow of gas and liquid into said separating chamber when said gas outlet is blocked;
said separated gas measuring means comprise probes disposed at a reference and at least one lower level in said separating chamber to signal collection of a preselected quantity of gas, and means for measuring the time required for that collection; and
the meter further includes a signal processor for utilizing the measured liquid flow rate and gas collection time to provide a gas concentration output signal.

* * * * *